United States Patent
Fukuda et al.

(10) Patent No.: US 8,545,898 B2
(45) Date of Patent: Oct. 1, 2013

(54) BROAD-SPECTRUM ANTIVIRAL COMPOSITION WITH EXCELLENT PRESERVATION STABILTY

(75) Inventors: Toshiaki Fukuda, Suita (JP); Koji Abe, Suita (JP); Takashi Shibata, Suita (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 289 days.

(21) Appl. No.: 12/527,338

(22) PCT Filed: Feb. 15, 2008

(86) PCT No.: PCT/JP2008/052493
§ 371 (c)(1),
(2), (4) Date: Sep. 30, 2009

(87) PCT Pub. No.: WO2008/099911
PCT Pub. Date: Aug. 21, 2008

(65) Prior Publication Data
US 2010/0028456 A1 Feb. 4, 2010

(30) Foreign Application Priority Data

Feb. 16, 2007 (JP) .................. 2007-036469

(51) Int. Cl.
*A01N 59/08* (2006.01)
*A61K 33/14* (2006.01)
(52) U.S. Cl.
USPC .......................................... 424/661; 424/600
(58) Field of Classification Search
None
See application file for complete search history.

(56) References Cited

U.S. PATENT DOCUMENTS

| | | | |
|---|---|---|---|
| 3,950,500 A * | 4/1976 | Jaszka | 423/480 |
| 6,200,557 B1 | 3/2001 | Ratcliff | |
| 2004/0104127 A1 | 6/2004 | Rojas | |

FOREIGN PATENT DOCUMENTS

| | | | |
|---|---|---|---|
| JP | 61-181532 A | | 8/1986 |
| JP | 11228316 A | * | 8/1999 |
| JP | 11-278808 A | | 10/1999 |
| JP | 11-278808 | * | 12/1999 |
| JP | 3110724 B2 | | 11/2000 |
| JP | 1999-278808 A | | 4/2001 |

OTHER PUBLICATIONS

Purogene Sales sheet, Downloaded from the internet on Oct. 20, 2011 from the URL: http://www.bio-cide.com/uploads/Purogene%20Sales%20Sheet.pdf.*
Purogene MSDS, Downloaded from the internet on Oct. 20, 2011 from the URL: http://www.aerosafe.com/media/Purogene.PDF.*
International Search Report of Application PCT/JP2008/052493 dated May 13, 2008.
Written Opinion of the International Searching Authority of Application PCT/JP2008/052493 dated May 13, 2008.
International Preliminary Report on Patentability dated Aug. 19, 2009.
Jun Wen Li et al., "Mechanisms of Inactivation of Hepatitis A Virus in Water by Chlorine Dioxide", Water Research, vol. 38, 2004 (month unknown), pp. 1514-1519, Elsevier.

(Continued)

*Primary Examiner* — James H Alstrum Acevedo
*Assistant Examiner* — Daniel L Branson
(74) *Attorney, Agent, or Firm* — Osha Liang LLP

(57) ABSTRACT

A composition for a broad-spectrum antiviral agent with excellent preservation stability, which comprises a pure chlorine dioxide solution comprising a chlorine dioxide gas dissolved therein, a chlorite, and a pH adjuster.

5 Claims, 7 Drawing Sheets

(56) References Cited

OTHER PUBLICATIONS

Yu-Shiaw Chen et al., "Inactivation of Human and Simian Dioxide", Applied and Environmental Microbiology, May 1990, pp. 1363-1366, vol. 56, No. 5, American Society for Microbiology.

Notice of Reasons for Refusal (Office Action) issued Jun. 9, 2010, issued by the Japan Patent Office in related Japan Patent Application No. JP-2008-558142, with English translation (6 pages).

Patent Disclosure No. 1999-278808, Patent Gazette (Previously cited in the International Search Report dated May 13, 2008, and filed in the IDS filed Sep. 30, 2009, with the USPTO).

Chen, Y.S., et al., "Applied and Environmental Microbiology", 1990, vol. 56, No. 5; pp. 1363-1366. (Previously cited in the International Search Report dated May 13, 2008, and filed in the IDS filed Sep. 30, 2009, with the USPTO).

Li, J.W., et al., "Water Research", 2004, vol. 38; pp. 1614-1519. (Previously cited in the International Search Report dated May 13, 2008, and filed in the IDS filed Sep. 30, 2009, with the USPTO).

Handbook of Japanese Pharmaceutical Excipients, Yakuji Nippo Ltd., 1994, the 1st Edition; pp. 150, 151, 246, 247, and 355. (Previously cited in the International Search Report dated May 13, 2008, and filed in the IDS filed Sep. 30, 2009, with the USPTO).

\* cited by examiner

Fig. 1

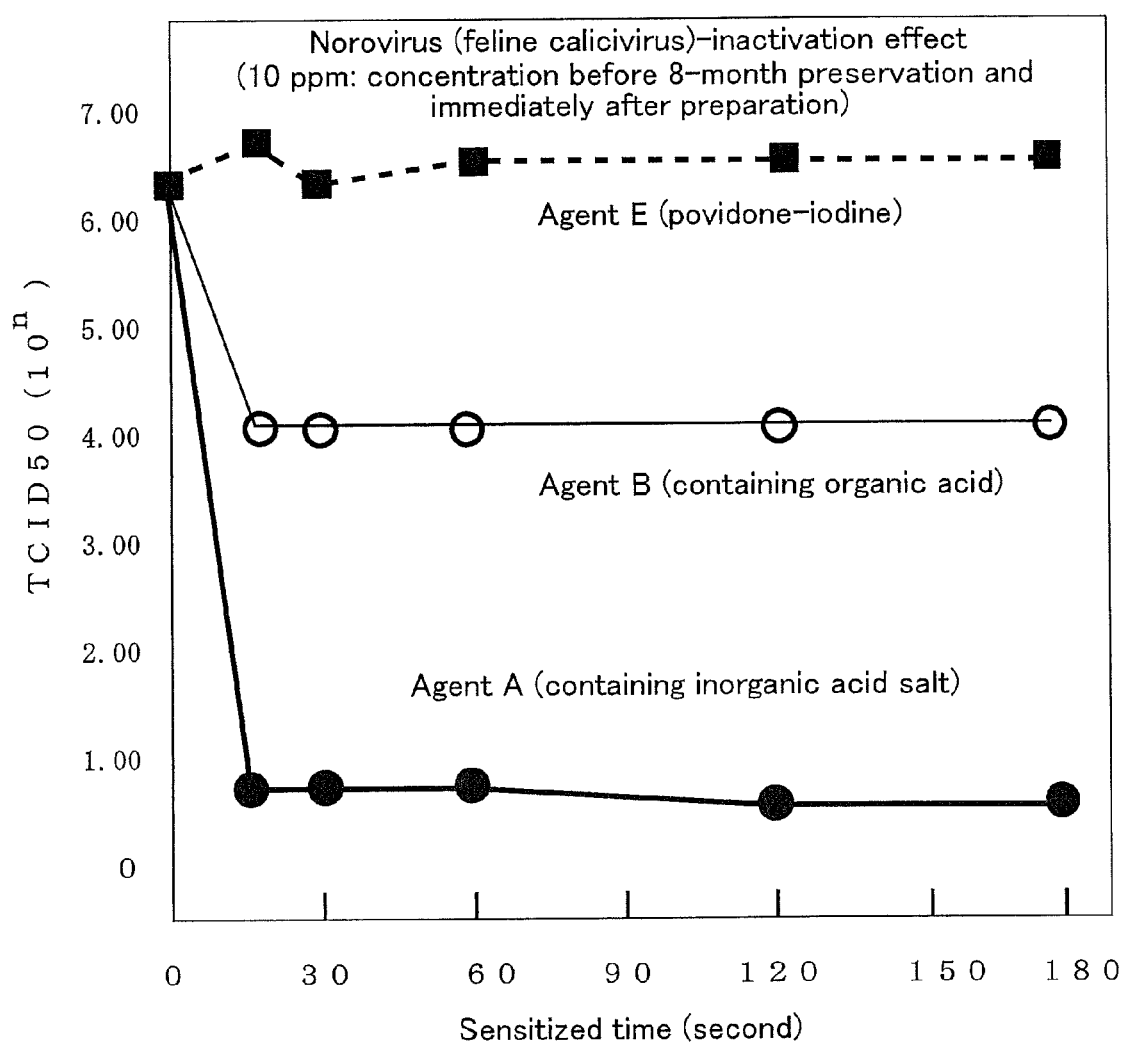

Coxsackievirus B5-inactivation effect (sensitized time: 1 minute)

[Graph showing TCID50 (log10) vs Agent concentration (0 ppm, 0.1 ppm, 1 ppm, 10 ppm, 100 ppm) for Agent A (containing inorganic acid salt), Agent B (containing organic acid), and Agent D (stabilized chlorine dioxide)]

(concentration before 8-month preservation and immediately after preparation)

(b)

Coxsackievirus B5-inactivation effect
(10 ppm: concentration before 8-month preservation and immediately after preparation)

[Graph showing TCID50 (log10) vs Sensitized time (0 minute, 1 minute, 2 minutes, 3 minutes) for Agent A (containing inorganic acid salt), Agent B (containing organic acid), and Agent C (Na hypochlorite)]

BROAD-SPECTRUM ANTIVIRAL COMPOSITION WITH EXCELLENT PRESERVATION STABILTY

TECHNICAL FIELD

The present invention relates to a composition for a broad-spectrum antiviral agent (hereinafter also simply referred to as "antiviral composition") with excellent preservation stability. Particularly, the present invention relates to an antiviral composition for an agent including chlorine dioxide dissolved therein, in which an antiviral activity is steadily retained for a long term, specifically, a pharmacological activity of chlorine dioxide during preservation does not change, and a chlorine dioxide concentration is not reduced even when dissolved chlorine dioxide dissipates by portions as chlorine dioxide gas during long-term preservation.

BACKGROUND ART

As is well known, chlorine dioxide gas is a strong oxidant, and because its oxidizing action is effective in sterilization and decomposition of malodorous substances, chlorine dioxide gas has been used in disinfectant, deodorant and the like. The chlorine dioxide gas is dissolved in water in 20 times its volume of water, to give a brown aqueous solution. From the viewpoint of easiness in handling, it is desirable to use chlorine dioxide in a form of such an aqueous solution.

When the aqueous solution of chlorine dioxide is brought into contact with air, chlorine dioxide gas is rapidly generated. Therefore, there has been proposed a technique in which chlorine dioxide gas is constantly generated while maintaining its stability, by dissolving chlorine dioxide gas in an aqueous solution of sodium peroxycarbonate, and thus by forming an aqueous solution containing sodium chlorite as a main component with retained alkalinity (pH 9), i.e., what is called a stabilized aqueous solution of chlorine dioxide (see Patent Document 1).

However, when the alkalinity is retained in the stabilized aqueous solution of chlorine dioxide, a generation amount of free chlorine dioxide gas having disinfecting and deodorizing effects or the like is extremely low, and thus the solution has a low pharmacological activity. Accordingly, it is difficult to attain satisfactory disinfecting and deodorizing effects or the like.

Therefore, in order to enhance the pharmacological activity of the stabilized aqueous solution of chlorine dioxide, an acid has been added immediately before its use to lower the pH to 7 or less, for generating chlorine dioxide gas.

However, with this technique in which an acid is added immediately before its use, there arise economical problems that processes and equipments or facilities to implement the processes are required in order to enhance the pharmacological activity of the stabilized aqueous solution of chlorine dioxide. In addition, since chlorine dioxide gas is rapidly generated as a result of the addition of acid, it is difficult to expect a sustained pharmacological activity of the stabilized aqueous solution of chlorine dioxide. Moreover, a pharmacological activity is not retained constant and sometimes reaches an extremely high level, which raises safety concern about effects on animals, especially on human being.

In order to solve the above-mentioned problems, there has been proposed a technique in which a mixture prepared by adding an organic acid, such as citric acid, to chlorite is blended with a dissolved chlorine dioxide solution, to thereby maintain a chlorine dioxide concentration nearly constant for a long term (see Patent Document 2). In this technique, carbon dioxide gas is not rapidly generated, and a desired pharmacological activity is sustained by maintaining the chlorine dioxide concentration constant for a long term. In addition, even when dissolved chlorine dioxide is continuously released by portions as chlorine dioxide gas, the chlorine dioxide concentration can be held in an approximately constant range.

Patent Document 1: Japanese Patent Application JP61-181532A
Patent Document 2: Japanese Patent JP3110724B

DISCLOSURE OF THE INVENTION

The present inventors made intensive and extensive studies with the view towards finding a novel clinical application of the chlorine dioxide solution including safe application to human being, which would be possible due to the improved preservation stability and controllable concentration. As a result, they discovered that the chlorine dioxide solution surprisingly exerts an inactivation effect against a wide range of viruses including a mucocutaneous infector virus, and that the solution retains an excellent potency (virus-inactivation potency) even after long-term preservation (for instance, after 1-year preservation in a container), and based on these findings, they completed the present invention.

Accordingly, the present invention provides a composition for a broad-spectrum antiviral agent with excellent preservation stability, which includes a chlorine dioxide solution.

To attain the above-described purpose, in a first aspect of the present invention, there is provided a composition for a broad-spectrum antiviral agent with excellent preservation stability which includes a pure chlorine dioxide solution including: a chlorine dioxide gas dissolved therein; a chlorite; and a pH adjuster.

In a second aspect of the broad-spectrum antiviral composition with excellent preservation stability of the present invention, the chlorite is sodium chlorite, and the pH adjuster is an inorganic acid or a salt thereof having a buffering property.

In a third aspect of the broad-spectrum antiviral composition with excellent preservation stability of the present invention, the chlorite is sodium chlorite, and the pH adjuster is phosphoric acid or a salt thereof.

In a fourth aspect of the broad-spectrum antiviral composition with excellent preservation stability of the present invention, the chlorite is sodium chlorite, and the pH adjuster is sodium dihydrogenphosphate or a mixture of sodium dihydrogenphosphate with sodium monohydrogenphosphate.

The antiviral composition of the present invention has an inactivation effect on a wide range of viruses, and though it contains chlorine dioxide, exhibits excellent preservation stability, and the viral inactivation effect is sustained after long-term preservation.

BRIEF DESCRIPTION OF DRAWINGS

FIG. 1 is a graph showing an influenza virus-inactivation effect of the broad-spectrum antiviral composition of the present invention.

FIG. 2 is a graph showing a norovirus (feline calicivirus as a surrogate)-inactivation effect of the broad-spectrum antiviral composition of the present invention.

FIG. 3 shows graphs indicating a coxsackievirus B5-inactivation effect of the broad-spectrum antiviral composition of the present invention in which (a) represents a case where the sensitized time is 1 minute, and (b) represents a case where the concentration is 10 ppm.

BEST MODE FOR CARRYING OUT THE INVENTION

Figure 4:
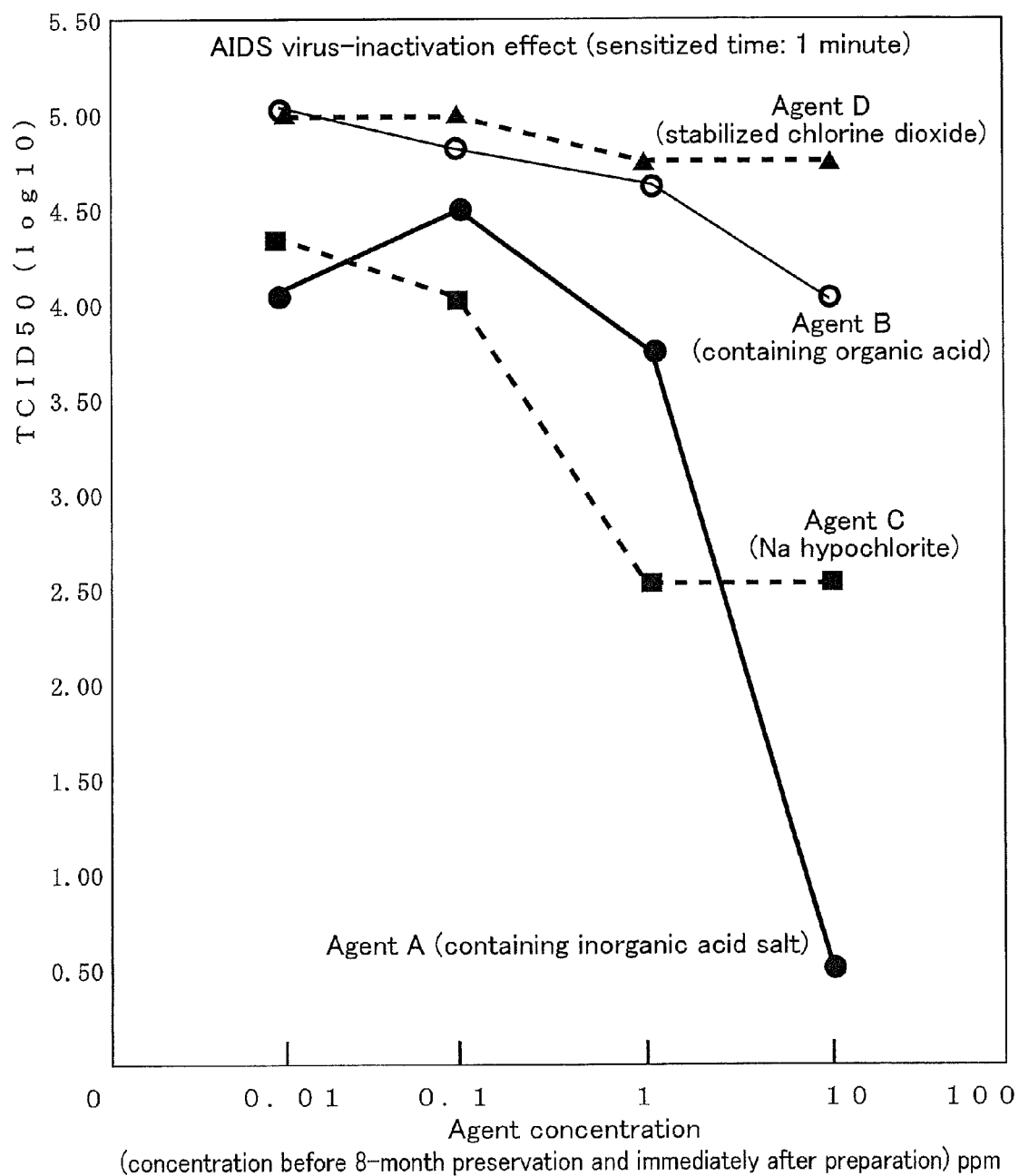
FIG. 4 is a graph showing an AIDS virus-inactivation effect of the broad-spectrum antiviral composition of the present invention.

An embodiment of the present invention will be described below, but the present invention should not be limited to this embodiment.

The composition for a broad-spectrum antiviral agent with excellent preservation stability of the present invention includes a pure chlorine dioxide solution including a chlorine dioxide gas dissolved therein, a chlorite, and a pH adjuster.

(Virus to be Inactivated)

For viruses to be inactivated by the antiviral composition of the present invention, a wide range of viruses can be mentioned, and examples include influenza virus (types A, B and C), avian influenza virus, norovirus (feline calicivirus), human papillomavirus (HPV: pathogen of condyloma acuminatum), coxsackievirus (pathogen of hand-foot-and-mouth disease, aseptic meningitis, summer cold, febrile disorder, paralysis and respiratory tract disease), AIDS virus (HIV), hepatitis B virus, canine parvovirus, rotavirus, HHV-1 (herpes simplex virus type 1 (HSV-1)), HHV-2 (herpes simplex virus type 2 (HSV-2)), HHV-3 (varicella-zoster virus (VZV)), HHV-5 (cytomegalovirus (CMV)), virus associated with an ophthalmic field (adenovirus for pharyngoconjunctival fever (pool fever) and epidemic keratoconjunctivitis (pink-eye); and enterovirus for acute hemorrhagic conjunctivitis).

(Chlorite)

For the chlorite to be used in the present invention, for example, salts of alkali metal chlorite and salts of alkali earth metal chlorite can be mentioned. Examples of the salt of alkali metal chlorite include sodium chlorite, potassium chlorite and lithium chlorite. Examples of the salt of alkali earth metal chlorite include calcium chlorite, magnesium chlorite and barium chlorite. Especially, not only from the viewpoint of availability, but also from the viewpoint of sustention of the pharmacological activity of chlorine dioxide, sodium chlorite and potassium chlorite are preferable, and sodium chlorite is most preferable.

(pH Adjuster)

For the pH adjuster to be used in the present invention, for example, organic acids and salts thereof, and inorganic acids and salts thereof can be mentioned. Examples of the organic acids and salts thereof include formic acid, acetic acid, propionic acid, butyric acid, lactic acid, pyruvic acid, citric acid, malic acid, tartaric acid, gluconic acid, glycolic acid, fumaric acid, malonic acid, maleic acid, oxalic acid, succinic acid, acrylic acid, crotonic acid, oxalic acid, glutaric acid, and salts thereof.

Examples of the inorganic acids include phosphoric acid, boric acid, metaphosphoric acid, pyrophosphoric acid, and sulfamic acid. Examples of the salts of the inorganic acid include sodium dihydrogenphosphate, and a mixture of sodium dihydrogenphosphate with sodium monohydrogenphosphate.

Especially, from the viewpoint of excellent preservation stability and thus excellent viral inactivation potency after long-term preservation, phosphoric acid and salts thereof are preferably used as the inorganic acid, and sodium dihydrogenphosphate is more preferably used.

It should be noted that one kind of the pH adjuster may be used alone or two or more kinds thereof may be used in combination. An acid having a pH of 4.5 to 6.5 as a 10% solution is preferably used, and an acid having a pH of 5.5 to 6.0 is more preferably used.

(Preparative Example of Chlorine Dioxide Solution)

The pure chlorine dioxide solution may be, for example, obtained in the following manner. Specifically, (a) a chlorite is dissolved in water to prepare 2,000 to 180,000 ppm of an aqueous chlorite solution, (b) chlorine dioxide gas is bubbled and dissolved in water to prepare 100 to 2,900 ppm of an aqueous solution of chlorine dioxide, and (c) a chlorite is dissolved in water to prepare 2,000 to 180,000 ppm of an aqueous chlorite solution, and in the solution is dissolved a pH adjuster in an amount of 0.5 to 100 g per 1,000 ml of the solution, to prepare an aqueous chlorite solution containing the pH adjuster.

Subsequently, 5.0 to 990 ml, preferably 50 to 300 ml of the aqueous solution of chlorous acid (item (a)), 5.0 to 990 ml, preferably 50 to 800 ml of the aqueous solution of chlorine dioxide (item (b)) and 5.0 to 990 ml, preferably 50 to 400 ml of the aqueous solution of chlorous acid containing the pH adjuster (item (c)) are mixed and stirred well at room temperature to thereby prepare a pure chlorine dioxide solution.

It should be noted that "pure chlorine dioxide" herein means that chlorine dioxide is present in a form of chlorine dioxide gas. It is preferred that the final pH of the pure chlorine dioxide solution is 4.5 to 6.5. When the pH is out of this range, the preservation stability was reduced, which may lead to fluctuation of the pharmacological activity during preservation, and to attenuation in the pharmacological activity after long-term (e.g. 2-year) preservation. In the present invention, more preferable pH range of the pure chlorine dioxide solution is 5.5 to 6.0.

Other Embodiment 1

In the embodiment described above, instead of the pH adjuster, an acidic surfactant may be used.

In this case, the broad-spectrum antiviral composition with excellent preservation stability includes a pure chlorine dioxide solution including a chlorine dioxide gas dissolved therein, a chlorite and an acidic surfactant.

In this case, the chlorite may be the same as those in the above-described embodiment, but from the viewpoint of sustention of the pharmacological activity of chlorine dioxide, sodium chlorite and potassium chlorite are preferable, and sodium chlorite is most preferable.

For the surfactant, those which make the pH of the pure chlorine dioxide solution from 4.5 to 6.5 are preferable, and those which make from 5.5 to 6.0 are more preferable.

Examples of the acidic surfactants include, but are not restricted to, a phosphoric acid ester salt surfactant (such as polyoxyethylene phosphoric acid ester and a salt of alkyl phosphoric acid ester), a sulfonic acid salt surfactant (such as alkyl or alkylbenzene sulfonate, e.g. sodium lauryl sulfonate and sodium dodecylbenzenesulfonate; alkylnaphthalene sulfonate, e.g. sodium isopropylnaphthalene sulfonate; and alkyl diphenyl ether sulfonate), a sulfuric acid ester salt surfactant (such as alkyl or alkylbenzene sulfate, oxyethylene alkyl phenyl ether sulfate, and polyoxyethylene alkyl phenyl ether sulfate), and a carboxylic acid salt surfactant (such as alkyl sulfosuccinate).

In addition, a mixed surfactant of sucrose fatty acid ester, sodium citrate, propylene glycol and ethanol, which is commercially available [Shokusen SE (manufactured by Mitsubishi-Kagaku Foods Corporation)], may be used.

For the surfactant, from the viewpoint of sustention of the pharmacological activity of chlorine dioxide, the mixed surfactant of sucrose fatty acid ester, sodium citrate, propylene glycol and ethanol is preferable.

Other Embodiment 2

In the embodiment described above, the pure chlorine dioxide solution including the chlorine dioxide gas dissolved therein, the chlorite and the pH adjuster may be mixed with a high water-absorbent resin and prepared as a gel-like composition.

In this case, the chlorite may be the same as those in the above-described embodiment, but from the viewpoint of sustention of the pharmacological activity of chlorine dioxide, sodium chlorite and potassium chlorite are preferable, and sodium chlorite is most preferable. The pH adjuster may also be the same as those in the above-described embodiment, but sodium dihydrogenphosphate and a mixture of sodium dihydrogenphosphate with sodium monohydrogenphosphate are preferable.

Examples of the high water-absorbent resin include a starch-containing water-absorbent resin (e.g., grafted starch-containing high water-absorbent resin, such as starch-acrylonitrile graft copolymer, starch-acrylic acid graft copolymer, starch-styrenesulfonic acid graft copolymer and starch-vinylsulfonic acid graft copolymer), a cellulose-containing water-absorbent resin (e.g., cellulose-containing high water-absorbent resin, such as cellulose-acrylonitrile graft copolymer, cellulose-styrenesulfonic acid graft copolymer, and cross-linked carboxymethyl cellulose; phosphoric-esterified paper and cloth; and carboxymethylated cloth), and a synthetic polymer-containing water-absorbent resin (e.g. polyvinyl alcohol-containing high water-absorbent resin, such as cross-linked polyvinyl alcohol; acrylic high water-absorbent resin, such as cross-linked polyacrylate, saponified polyacrylonitrile-containing polymer and cross-linked polyethylene glycol dimethacrylate; and cross-linked polyethylene oxide-containing high water-absorbent resin).

Examples of those commercially available include a starch/polyacrylic acid resin [Aqualic (powder, manufactured by Nippon Shokubai, Co., Ltd.), Sanwet (powder, manufactured by Sanyo Chemical Industries Ltd.)], a cross-linked polyacrylic acid resin [Arasorb (powder, manufactured by Arakawa Chemical Industries, Ltd.), Wondergel (powder, manufactured by Kao Corporation), Aqua Keep (powder, manufactured by Sumitomo Seika Chemicals, Co., Ltd.), Diawet (powder, manufactured by Mitsubishi Petrochemical Co., Ltd.)], an isobutylene/maleic acid resin [KI gel (powder, manufactured by Kuraray Co., Ltd.)], and a poval/polyacrylic acid salt resin [Sumikagel (powder, manufactured by Sumitomo Chemical Co., Ltd.)]. Use of these will not hinder the present invention.

In the case where the gel-like composition is obtained by admixing with the high water-absorbent resin, for example, 50 to 99 weight % of the pure chlorine dioxide solution prepared in the above-described manner is added to 1.0 to 50 weight % of the high absorbent resin (powder), and stirred well at room temperature. Such a "gel-like composition" may be, for example, of general utility as being filled in a container having an opening on at least one side (see Japanese Patent Application JP61-40803A), or alternatively, of general utility as being filled in a container formed of paper or nonwoven fabric containing synthetic fiber as constituent fiber, with rims thereof sealed by heat-sealing the synthetic fiber or by a synthetic-resin adhesive. Examples of the synthetic fiber include the conventional thermoplastic synthetic fiber, such as polypropylene fiber, polyester fiber and polyamide fiber. In the case of the container formed of paper or nonwoven fabric containing such synthetic fiber as constituent fiber, it is possible to prevent clogging of the container which may otherwise be caused by the attached "gel-like composition", and at the same time to sustainably evaporate chlorine dioxide from the "gel-like composition".

Other Embodiment 3

In the embodiment described above, instead of the pH adjuster, an acidic high water-absorbent resin may be used. In this case, the dissolved chlorine dioxide gas and the chlorite are contained in the resin, which gives a gel-like composition.

In this case, the chlorite may be the same as those in the above-described embodiment, but from the viewpoint of sustention of the pharmacological activity of chlorine dioxide, sodium chlorite and potassium chlorite are preferable, and sodium chlorite is most preferable.

For the high water-absorbent resin, those which make the pH of the pure chlorine dioxide solution from 4.5 to 6.5 are preferable, and those which make from 5.5 to 6.0 are more preferable.

Examples of the acidic high water-absorbent resin include, but are not restricted to, sodium salt cross-linkage in the acrylic acid polymerization [Aqualic (manufactured by Nippon Shokubai, Co., Ltd.)] commercially available.

Other Embodiment 4

In the embodiment described above, the pure chlorine dioxide solution including the chlorine dioxide gas dissolved therein, the chlorite and the pH adjuster may be mixed with a foam agent, which gives a foaming composition.

In this case, the chlorite may be the same as those in the above-described embodiment, but from the viewpoint of sustention of the pharmacological activity of chlorine dioxide, sodium chlorite and potassium chlorite are preferable, and sodium chlorite is most preferable. The pH adjuster may also be the same as those in the above-described embodiment, but sodium dihydrogenphosphate and a mixture of sodium dihydrogenphosphate with sodium monohydrogenphosphate are preferable.

The foam agent may be formed of a surfactant and a foam stabilizer, or of a surfactant, a foam stabilizer and an aerosol propellant.

Examples of the surfactant include, but are not restricted to, (1) at least one anionic surfactant selected from: a carboxylate salt, such as polyoxyethylene alkyl ether carboxylate; a sulfonate salt, such as alkylbenzenesulfonate and alkylnaphthalenesulfonate; a salt of sulfuric acid ester, such as salt of sulfuric acid higher alcohol ester; and a salt of phosphoric acid ester, such as polyoxyethylene alkyl ether phosphate, (2) a cationic surfactant, such as fatty acid quaternary ammonium salt, (3) a carboxybetaine type ampholytic surfactant, (4) a nonionic surfactant, such as polyoxyethylene alkyl ether, polyoxyethylene glycerin fatty acid ester, polyethylene glycol fatty acid ester, and fatty acid alkanolamide, (5) a fluorine-containing surfactant, and (6) a saponin.

Examples of the foam stabilizer include, but are not restricted to, (7) a stabilizer prepared by adding mono- or di-ethanolamine to the above-mentioned anionic surfactant, (8) a stabilizer prepared by adding a long-chain alcohol or alkylsulfoxide to the above-mentioned nonionic surfactant, and (9) liquid paraffin.

Examples of the aerosol propellant include, but are not restricted to, a high-pressure gas with low toxicity, such as liquefied natural gas (LPG), liquefied butane and dimethyl ether.

In the case where the foaming composition is prepared by adding the foam agent, the foaming composition may be prepared, for example, in a closed container, by adding 5.0 to 20 weight % of the foaming agent and 60 to 95 weight % of the surfactant to 1.0 to 20 weight % of the pure chlorine dioxide solution as prepared above and stirring the mixture well at room temperature. Such a "foaming composition" may be enclosed in, for example, a trigger type foaming container, a pump type foaming container or the like.

EXAMPLES

Example 1

Preparation of Agent A

In the following manner, a chlorine dioxide solution was prepared. Specifically, to 250 ml of water in which 2,000 ppm of chlorine dioxide gas had been dissolved were added 680 ml of water and 80 ml of a 25% solution of sodium chlorite, and stirred. Subsequently, to the solution was added sodium dihydrogenphosphate in such an amount that the pH of the solution became 5.5 to 6.0 and stirred, to thereby obtain 1,000 ml of a chlorine dioxide solution including chlorine dioxide gas dissolved therein, sodium chlorite, and sodium dihydrogenphosphate.

Example 2

Preparation of Agent B

A chlorine dioxide solution as a control was prepared in the same manner as in Example 1, except that citric acid as organic acid was used instead of sodium dihydrogenphosphate (a salt of an inorganic acid having a buffering property).
<Antiviral Testing (Virus-Inactivation Test After 8-Month Preservation)>

For the antiviral testing, various concentrations of the chlorine dioxide solutions (agent A, agent B) were prepared and left in respective containers made of synthetic resin for 8 months. Specifically, each of the chlorine dioxide solutions obtained in each of Examples 1 and 2 was placed in a container having an opening with a diameter of 2 cm, and after closing a screw-cap, the container was left at room temperature for 8 months. Subsequently, an antiviral activity effect of the solution was examined. As controls, sodium hypochlorite (agent C), stabilized chlorine dioxide (sodium chlorite) (agent D), and povidone-iodine (agent E) were used. The agents C to E were not preserved for 8 months, and subjected to the test immediately after the purchase. The agents used in the test are summarized in Table 1.

TABLE 1

| Agent A | Chlorine dioxide solution (containing inorganic acid salt) obtained in Example 1 |
| Agent B | Chlorine dioxide solution (containing organic acid) obtained in Example 2 |
| Agent C | Sodium hypochlorite |
| Agent D | Stabilized chlorine dioxide (sodium chlorite) |
| Agent E | Povidone-iodine |

(1) Antiviral Testing (Influenza Virus)

Figure 1:
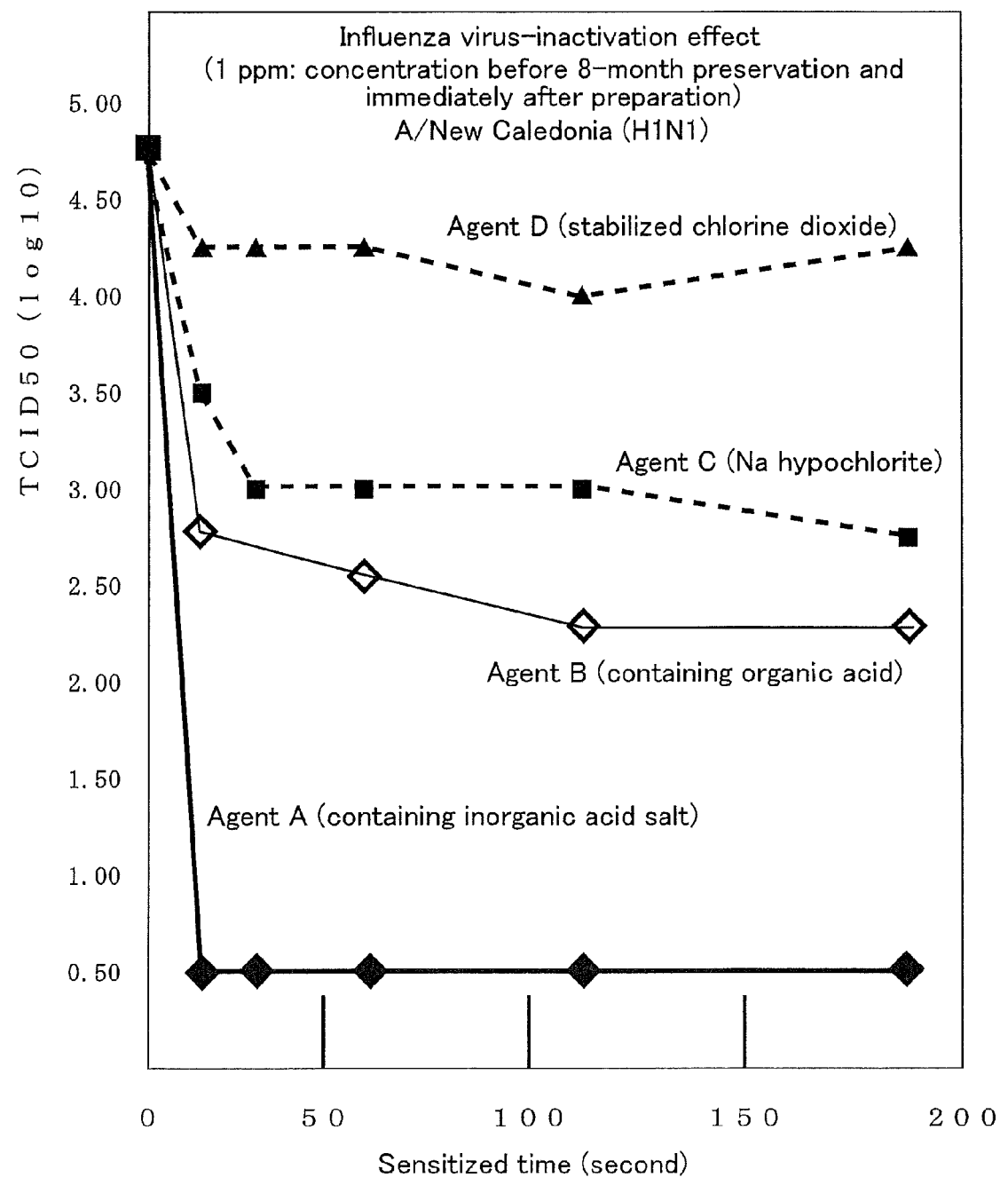

To each agent (see Table 1) was added influenza virus (A/New Caledonia (H1N1)) strain, and after a designated sensitized time elapsed, the agent was neutralized with a sodium thiosulfate solution, and a 10-fold dilution series was prepared. Host cells (MDCK cell (canine renal epithelial-derived established cell line)) which had been incubated at 37° C. under 5% $CO_2$ for 3 days were inoculated with the 10-fold dilution series in a microplate (96 wells), and cultured for 5 days. TCID50 (50% Tissue Culture Infective Dose) (log 10) was calculated using a cytopathogenic effect (CPE) by virus as a criterion, to thereby evaluate an antiviral activity effect of the agent. As a control, one diluted with distilled water, instead of the agent, was used. The results are shown in FIG. 1.

As is apparent from FIG. 1, the antiviral composition of the present invention exhibited a remarkable inactivation effect against influenza virus even after 8-month preservation, and the composition at a concentration of 1 ppm with a sensitized time of 15 seconds was 1,000 or more times as effective as sodium hypochlorite.

In the antiviral composition of the present invention, the pH adjuster is used as one component. It was also elucidated that, when the inorganic acid (sodium dihydrogenphosphate) is used for this pH adjuster rather than the organic acid, a viral inactivation effect is drastically (remarkably) improved.

(2) Antiviral Testing (Norovirus)

Each agent was added to a feline calicivirus FCV-F4 strain, which is a surrogate virus for norovirus. A CRFK cell (feline renal-derived established cell line) was used as host cell, and a test was performed in the same manner as in the antiviral testing (1). TCID50 (log 10) was calculated using a cytopathogenic effect (CPE) by virus as a criterion, to thereby evaluate the antiviral activity effect of the agent. The results are shown in FIG. 2.

As is apparent from FIG. 2, the antiviral composition of the present invention exhibited a remarkable inactivation effect against feline calicivirus as a surrogate virus for norovirus, even after 8-month preservation, and an anti-feline calicivirus activity at a concentration of 10 ppm with a sensitized time of 15 seconds was 1 million times as large as that of povidone-iodine. The difference in the levels of the anti-feline calicivirus activity did not change even after 3 minutes.

(3) Antiviral Testing (Coxsackievirus B5)

Each agent was added to coxsackievirus B5 (hand-foot-and-mouth disease), an LLCMK2 cell was used as host cell, and a test was performed in the same manner as in the antiviral testing (1). TCID50 (log 10) was calculated using a cytopathogenic effect (CPE) by virus as a criterion, to thereby evaluate the antiviral activity effect of the agent. The results are shown in FIG. 3(a),(b).

As is apparent from FIG. 3(a),(b), the antiviral composition of the present invention exhibited a remarkable inactivation effect against coxsackievirus B5 (hand-foot-and-mouth disease) and the composition at a concentration of 10 ppm with a sensitized time of 1 minute was 32 times more effective, or of 2 minutes was 100 times more effective, than sodium hypochlorite.

(4) Antiviral Testing (HIV)

Each agent was added to HIV (LAV strain), an MT-4 cell was used as host cell, and a test was performed in the same manner as in the antiviral testing (1), following a protocol of the known viral infection test. TCID50 (log 10) was calculated using a cytopathogenic effect (CPE) by virus as a criterion, to thereby evaluate the antiviral activity of the agent. The results are shown in FIG. 4.

As is apparent from FIG. 4, the antiviral composition of the present invention exhibited a remarkable inactivation effect against HIV (LAV strain) and the composition at a concentration of 10 ppm with a sensitized time of 1 minute was 100 or more times as effective as sodium hypochlorite (the value became less than the detection limit).

(5) Antiviral Testing (Human Hepatitis B Surface Antigen (HBsAg))

Each agent was added to human hepatitis B surface antigen (HBsAg), and after 1, 2, 3 or 4 days of sensitization, the agent was neutralized with a sodium thiosulfate solution, and HBsAg titer was measured using a chemiluminescent immunoassay "Architect-HBsAg (manufactured by Dainabot Co., Ltd.)". An anti-HBsAg activity of the agent was evaluated. The results are shown in FIG. 5.

Figure 5:
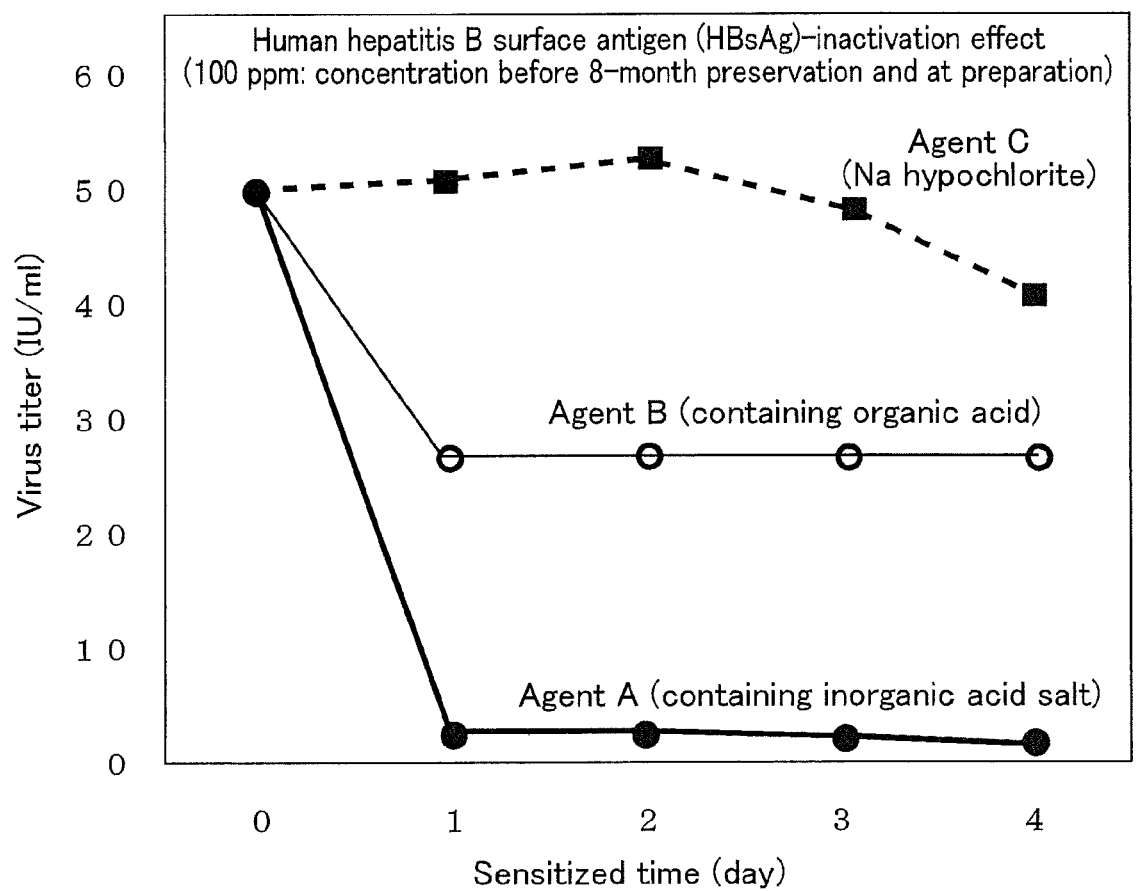
FIG. 5 is a graph showing a hepatitis B virus-inactivation effect of the broad-spectrum antiviral composition of the present invention.

As is apparent from FIG. 5, the antiviral composition of the present invention exhibited a remarkable anti-HBsAg activity against HBsAg. When the untreated group with an antigen titer of 54 IU/ml was treated with the composition at the concentration of 100 ppm, the antigen titer of 1 IU/ml, 0.2 IU/ml, 0.1 IU/ml and less than the detection limit were observed for sensitized times of 1 day, 2 days, 3 days and 4 days, respectively, indicating the presence of an anti-HBsAg activity. On the other hand, when treated with sodium hypochlorite at the concentration of 100 ppm, the antigen titer of 50 IU/ml, 51 IU/ml, 51 IU/ml and 49 IU/ml were observed for 1 day, 2 days, 3 days and 4 days, respectively, indicating the absence of an anti-HBsAg activity.

(6) Antiviral Testing (Canine Parvovirus <CPV(Y-1)>)

Figure 6:
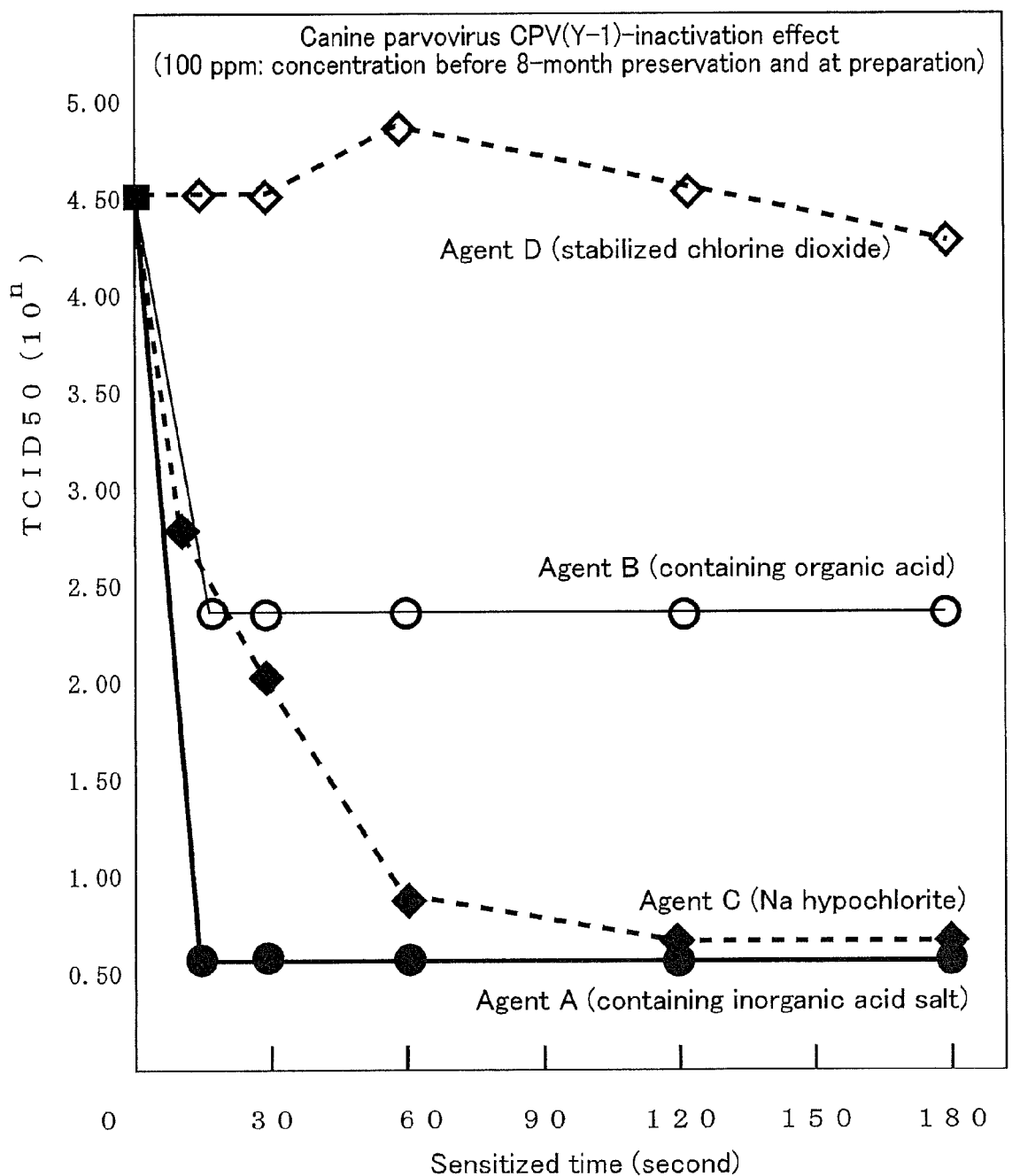
FIG. 6 is a graph showing a canine parvovirus-inactivation effect of the broad-spectrum antiviral composition of the present invention.

Each agent was added to canine parvovirus <CPV(Y-1)>, a CRFK cell (feline renal-derived established cell line) was used as host cell, and a test was performed in the same manner as in the antiviral testing (1), and cultured for 7 days. A swine hemagglutination test was performed on the culture solution, and a test solution observed with hemagglutination was considered as CPV infection, and TCID50 was obtained. The results are shown in FIG. 6 (the present test was adopted due to difficulties in observation of cytopathogenic effect (CPE)).

With respect to the antiviral activity against CPV of the antiviral composition of the present invention, the infectivity titer decreased by 99.99% or more (thus to the detection limit or less) after 120 seconds and 180 seconds in the case of the concentration of 10 ppm, and within 15 seconds in the case of 100 ppm.

On the other hand, with respect to the sodium hypochlorite solution, the infectivity titer remained at 100 TCID50 after 180 seconds in the case of 10 ppm, and decreased by 99.99% or more (thus to the detection limit or less) after 120 seconds in the case of 100 ppm. With respect to the stabilized chlorine dioxide solution, no decrease in the infectivity titer was observed after 180 seconds, even in the case of 100 ppm.

The antiviral activity of the antiviral composition of the present invention was approximately 10 times more than that of the sodium hypochlorite solution.

(7) Antiviral Testing (Rotavirus)

Figure 7:
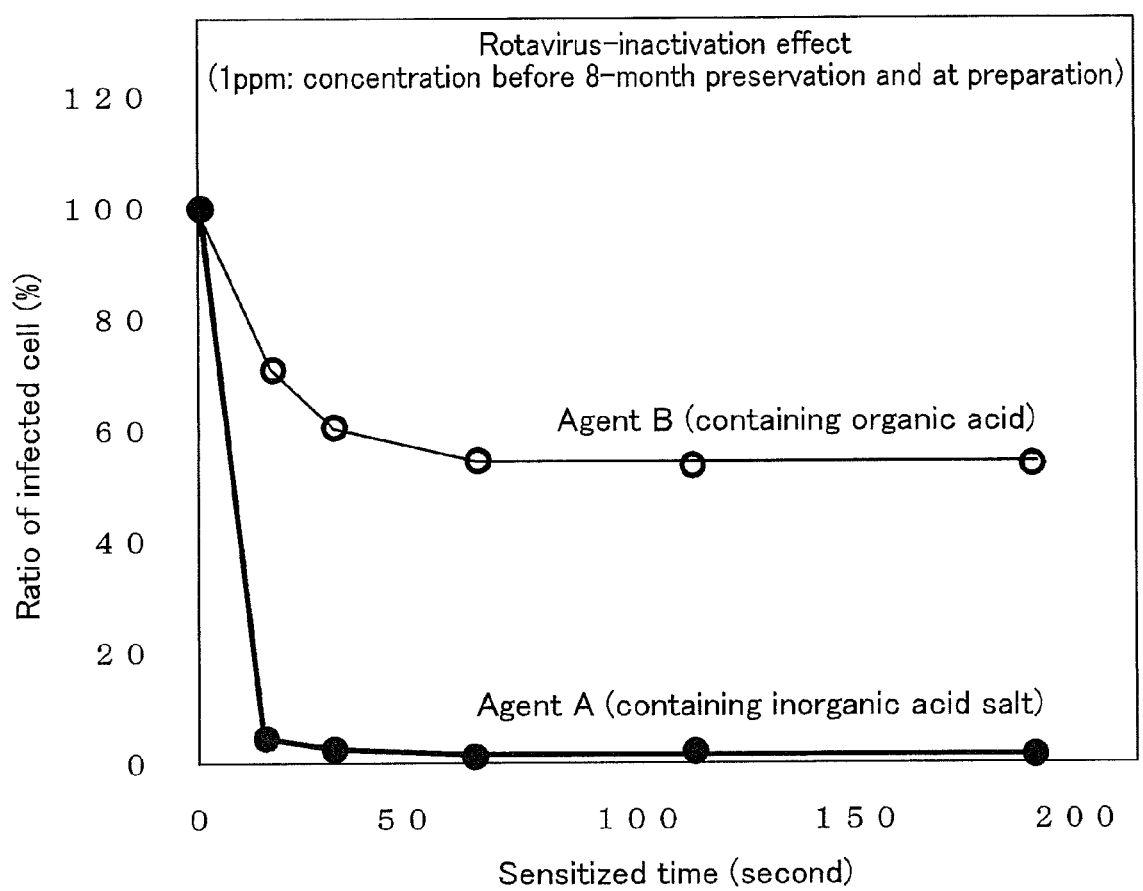
FIG. 7 is a graph showing a rotavirus-inactivation effect of the broad-spectrum antiviral composition of the present invention.

An agent was prepared so that the final concentration became 1 ppm, and was mixed with human rotavirus (Wa strain). Fifteen to 180 seconds after the mixing, an MA-104 cell was inoculated with the mixture and cultured in accordance with a common protocol. A number of cells observed with viral proliferation, i.e. number of cells showing positive FITC fluorescent was counted using a fluorescent antibody method, and an average value (N=4) was obtained, which was multiplied by a dilution factor. The calculation result of the viral antiproliferative effect was obtained as a ratio (%) of a cell number with the agent-treated virus proliferation to a cell number with the untreated virus proliferation, for each agent concentration and each treating time. The results are shown in FIG. 7.

When rotavirus was treated with the antiviral composition of the present invention at 10.0 ppm and 1.0 ppm for 15 seconds, the ratios indicating the viral proliferation were decreased to 0.3% or less and 2.1% or less, respectively, as compared with the case of the untreated virus. When treated at 0.1 ppm for 30 seconds and at 0.01 ppm for 60 seconds, the ratios were decreased to 8.4% or less and 16.4% or less, respectively.

(8) Antiviral Testing (Human Papillomavirus)

To an affected area of a male diagnosed as infected with condyloma acuminatum (causative virus: human papillomavirus), an appropriate amount of the antiviral composition of the present invention (concentration: 100 ppm) was applied three times a day. One day after the application, white indurations in the affected area turned into red indurations. Two days later, the affected area became smaller, and three days later, turned into scab and eventually disappeared.

(Discussion)

As described above, it was elucidated that the antiviral composition of the present invention has an inactivation activity on a wide range of viruses even after 8-month preservation. Moreover, since the composition is effective even at a low concentration, adversary effect (e.g. stimulation) on human body, especially skin mucosa, can be suppressed to a minimum, and thus clinically suitably used as a therapeutic agent for mucocutaneous viral infectious disease. It is also noted from the above-described test results that a higher viral inactivation activity can be obtained when the inorganic acid or salt thereof is used as the pH adjuster in preparation of the antiviral composition of the present invention, as compared with the organic acid.

Furthermore, the followings can be noted. Specifically, in the antiviral composition of the present invention, excellent preservation stability can be obtained. For example, the dissolved chlorine dioxide concentration can be maintained constant for a long term, that is, even when chlorine dioxide is continuously released by portions as gas from the antiviral composition (or even when chlorine dioxide gas is aggressively kept released), the chlorine dioxide concentration in the antiviral composition can be held in an approximately constant range. The expression "continuously released by portions as gas" herein means that, for example, during transportation or preservation, even though a lid of a container is closed, chlorine dioxide dissipates as gas in the course of nature, and the expression "chlorine dioxide gas is aggressively kept released" herein means that chlorine dioxide gas is released to a gas phase with an expectation of obtaining an antiviral activity in the gas phase.

When phosphoric acid or salt thereof is used as an inorganic acid or a salt thereof having a buffering property, as compared with other inorganic acids or organic acids, the preservation stability is further improved (period with the preservation stability is further extended), and fluctuation (change) in a liquid property (pH) over time during preservation is suppressed.

Moreover, by selecting sodium dihydrogenphosphate or the mixture of sodium dihydrogenphosphate with disodium hydrogenphosphate from among numerous inorganic acids or salts thereof, and by combining this with sodium chlorite, an excessive progression of a reaction in which sodium chlorite turns into chlorine dioxide hardly occurs, and thus a gas equilibration state is retained by replenishing chlorite ion from sodium chlorite that compensates only chlorine dioxide that is lost by natural decomposition or that dissipates from a lid portion or walls of the container. As described above, the present invention is suitable in that unnecessary consumption of sodium chlorite is suppressed and sodium chlorite is efficiently consumed, leading to further improvement in the preservation stability (period with the preservation stability is further extended), and to further suppression of fluctuation (change) in the chlorine dioxide concentration over time during preservation (both the decrease and increase in the concentration can be suppressed). In addition, a mechanism of the antiviral composition for replenishing chlorine atom from sodium chlorite for a long term is exerted even in a space or on a subject, to which the antiviral composition is applied, sprayed or diffused. This provides an excellent sustained effect, i.e. lasting antiviral activity after application, spraying or diffusion of the antiviral composition.

INDUSTRIAL APPLICABILITY

The broad-spectrum antiviral composition of the present invention can be used for inactivating various types of viruses.

The invention claimed is:

1. A composition for a broad-spectrum antiviral agent remaining stable after storage for a period of eight months, which comprises a chlorine dioxide solution obtained by mixing:
   (a) 5.0 to 990 arts by 2,000 to 180,000 ppm aqueous chlorite solution;
   (b) 5.0 to 990 parts by volume of a 100 to 2,900 ppm aqueous chlorine dioxide solution; and
   (c) 5.0 to 990 parts by volume of a 2,000 to 180,000 ppm aqueous chlorite solution that contains a pH adjuster in an amount of 0.5 to 100 g per 1,000 ml of the solution, wherein the pH adjuster comprises phosphoric acid, a salt of phosphoric acid, or a combination thereof;
   provided that the chlorine dioxide solution does not comprise citric acid.

2. The composition according to claim 1, wherein
   the chlorite is sodium chlorite, and
   the pH adjuster is sodium dihydrogenphosphate or a mixture of sodium dihydrogenphosphate with sodium monohydrogenphosphate.

3. The composition according to claim 1, wherein a pH of the solution is in a range of 4.5 to 6.5.

4. The composition according to claim 3, wherein the pH of the solution is between 5.5 and 6.0.

5. The composition according to claim 1, wherein the chlorine dioxide solution obtained by mixing;
   (a) 50 to 300 parts by volume of a 2,000 to 180,000 ppm aqueous chlorite solution;
   (b) 50 to 800 parts by volume of a 100 to 2,900 ppm aqueous chlorine dioxide solution; and
   (c) 50 to 400 parts by volume of a 2,000 to 180,000 ppm aqueous chlorite solution that contains a pH adjuster in an amount of 0.5 to 100 g per 1,000 ml of the solution, wherein the pH adjuster comprises selected from phosphoric acid, a salt of phosphoric acid, or a combination thereof;
   provided that the chlorine dioxide solution does not comprise citric acid.

* * * * *

UNITED STATES PATENT AND TRADEMARK OFFICE
CERTIFICATE OF CORRECTION

PATENT NO.        : 8,545,898 B2  
APPLICATION NO.   : 12/527338  
DATED             : October 1, 2013  
INVENTOR(S)       : Toshiaki Fukuda et al.

Page 1 of 1

It is certified that error appears in the above-identified patent and that said Letters Patent is hereby corrected as shown below:

On the title page, item (54) and in the specification, column 1, there is a typographical error in the Title: "BROAD-SPECTRUM ANTIVIRAL COMPOSITION WITH EXCELLENT PRESERVATION STABILTY" should read:

-- BROAD-SPECTRUM ANTIVIRAL COMPOSITION WITH EXCELLENT PRESERVATION STABILITY --.

In the Claims:

At column 11, claim number 1, line number 30, "(a) 5.0 to 990 arts by 2,000 to 180,000 ppm aqueous chlorite solution;" should read:

-- (a) 5.0 to 990 parts by volume of a 2,000 to 180,000 ppm aqueous chlorite solution; --.

Signed and Sealed this  
Twenty-eighth Day of January, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,545,898 B2 | Page 1 of 1 |
| APPLICATION NO. | : 12/527338 | |
| DATED | : October 1, 2013 | |
| INVENTOR(S) | : Fukuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this
Second Day of December, 2014

Michelle K. Lee
*Deputy Director of the United States Patent and Trademark Office*